(12) United States Patent
Feenstra et al.

(10) Patent No.: US 7,126,903 B2
(45) Date of Patent: Oct. 24, 2006

(54) VARIABLE FOCUS LENS

(75) Inventors: Bokke Johannes Feenstra, Eindhoven (NL); Stein Kuiper, Eindhoven (NL); Sjoerd Stallinga, Eindhoven (NL); Bernardus Hendrikus Wilhelmus Hendriks, Eindhoven (NL); Rudolph Maria Snoeren, Eindhoven (NL)

(73) Assignee: Koninklijke Philips Electronics N. V., Eindhoven (NL)

( * ) Notice: Subject to any disclaimer, the term of this patent is extended or adjusted under 35 U.S.C. 154(b) by 290 days.

(21) Appl. No.: 10/504,241

(22) PCT Filed: Jan. 24, 2003

(86) PCT No.: PCT/IB03/00222

§ 371 (c)(1),
(2), (4) Date: Aug. 10, 2004

(87) PCT Pub. No.: WO03/069380

PCT Pub. Date: Aug. 21, 2003

(65) Prior Publication Data

US 2005/0113912 A1      May 26, 2005

(30) Foreign Application Priority Data

Feb. 14, 2002  (EP)  ................... 02075649

(51) Int. Cl.
*G11B 7/00* (2006.01)
*G02F 1/03* (2006.01)
(52) U.S. Cl. .................. 369/112.23; 359/253
(58) Field of Classification Search ............... None
See application file for complete search history.

(56) References Cited

U.S. PATENT DOCUMENTS

2001/0017985 A1 *  8/2001  Tsuboi et al. ............. 396/506
2002/0176148 A1 * 11/2002  Onuki et al. ............. 359/253

FOREIGN PATENT DOCUMENTS

| JP | 2002-169005 | * | 6/2002 |
| WO | WO/9918456 | * | 4/1999 |
| WO | WO/0058763 | * | 10/2000 |

* cited by examiner

Primary Examiner—Paul W. Huber

(57) ABSTRACT

A variable focus lens comprising a first fluid (A) and a second, non-miscible, fluid (B) in contact over a meniscus. A first electrode (2) separated from the fluid bodies by a fluid contact layer (10), and a second electrode (12) in contact with the first fluid to cause an electrowetting effect whereby the shape of the meniscus is altered. The fluid contact layer has a substantially cylindrical inner wall.

16 Claims, 2 Drawing Sheets

VARIABLE FOCUS LENS

This application is a 371 of PCT/IB03/00222, filed Jan. 24, 2003.

This invention relates to a variable focus lens comprising a first fluid and a second fluid which are in contact over a meniscus and to a method of operating such a variable focus lens. The shape of the meniscus can be controlled by a voltage.

A fluid is a substance that alters its shape in response to any force, that tends to flow or to conform to the outline of its chamber, and that includes gases, liquids and mixtures of solids and liquids capable of flow.

The meniscus between the first fluid and the second fluid is called concave, if the meniscus is hollow as seen from the second fluid. If the first fluid is regarded as a lens, this lens would normally called concave if the meniscus is concave according to the definition in the previous sentence.

A variable focus lens having such an arrangement is described in International patent application WO 99/18456. In this arrangement, the lens comprises a chamber filled with a conductive first liquid, a droplet of an insulating, non-miscible second liquid being held in a surface zone of the chamber wall by a fluid contact layer applied on the wall. The fluid contact layer positions the droplet because part of the fluid contact layer is hydrophobic and an adjacent part is hydrophilic. Application of a voltage to electrodes in the chamber causes the refracting upper surface or meniscus of the droplet to become more convex. In one embodiment, the hydrophobic and hydrophilic parts of the fluid contact layer are arranged along a cylindrical surface, the sides of the droplet being positioned axially along the cylindrical surface, and thereby centred, by the hydrophilic part when no voltage is applied and by a series of electrodes along the sides of the cylinder when a voltage is applied. Such a lens is complex to manufacture and, particularly in the cylindrical configuration, requires a relatively high voltage in order to alter the lens characteristics of the droplet, which can cause premature degradation of the lens when used over a period of time.

A further variable focus lens having such an arrangement is described in the international patent application WO 00/58763. The proposed means for centring a droplet of insulating liquid is a bell-mouthed recess formed of an insulating layer in an adjustable lens. The sides of the recess are arranged so as to keep the droplet centred within the recess and to provide a convex refracting surface on the droplet. The recess is shaped such that the manufacture of such a lens remains relatively complex, and since the base of the recess is formed of the same material as the sides of the recess, such material must be chosen to be transparent if the lens is to be operative.

In accordance with the present invention, there is provided a variable focus lens including a substantially cylindrical fluid chamber having a cylinder wall and an axis, the fluid chamber including a first fluid (A) and an axially displaced second fluid (B), the fluids being non-miscible, in contact over a meniscus and having different indices of refraction, a fluid contact layer arranged on the inside of the cylinder wall, a first electrode separated from the first fluid and second fluid by the fluid contact layer, a second electrode acting on the second fluid, the fluid contact layer having a wettability by the second fluid which varies under the application of a voltage between the first electrode and the second electrode, such that the shape of the meniscus varies in dependence on the said voltage, wherein the wettability of the fluid contact layer by the second fluid is substantially equal on both sides of the intersection of the meniscus with the contact layer when no voltage is applied between the first and second electrodes.

The equal wettability of the fluid contact layer on both sides of the intersection allows a larger movement of the meniscus and, as a consequence, a greater change in curvature of the meniscus. It allows a concave meniscus to become convex or vice versa.

In a preferred embodiment the lens is arranged to produce a meniscus shape which is concave, the shape becoming less concave at increasing magnitude of voltage applied between the first and second electrodes. With the fluid contact layer substantially cylindrical, the tendency of the first fluid to wet the fluid contact surface can be used to produce the concave meniscus shape, and furthermore, relatively low voltages can be used to vary the meniscus shape to alter the power of the lens. Thereby, a desired range in lens power may be produced without the application of excess voltage.

By using a substantially cylindrical inner surface of the fluid contact layer and arranging the lens to produce a concave meniscus shape, the range in lens power of the lens can be improved without the application of excess voltage. At sufficiently high magnitude of voltage the shape of the meniscus may become convex. Application of excess voltage can lead to the charging of the fluid contact layer, which has been found to cause degradation of the layer, leading to a significant reduction in the useful lifetime of the lens.

A substantially cylindrical inner surface for the fluid contact layer may be produced without the need for complex processing techniques. In particular, such an inner surface shape may be produced by dip coating of a cylindrical electrode, which is a relatively reliable and inexpensive procedure. The fluid contact layer is furthermore preferably of a uniform thickness so as to provide a reliable refractive behaviour of the meniscus throughout the adjustable range of the lens. Again, such a uniform fluid contact layer can be readily produced by dip coating a cylindrical electrode element.

A second aspect of the invention relates to a method of operating a variable focus lens including a substantially cylindrical fluid chamber having a cylinder wall, the fluid chamber including a first fluid (A) and an axially displaced second fluid (B), the fluids being non-miscible, in contact over a meniscus and having different indices of refraction, a fluid contact layer arranged on the inside of the cylinder wall, a first electrode separated from the first fluid and second fluid by the fluid contact layer, a second electrode acting on the second fluid, the wettability of the fluid contact layer by the second fluid being substantially equal on both sides of the intersection of the meniscus with the contact layer when no voltage is applied between the first and second electrodes, the wettability of the fluid contact layer by the second fluid varying under the application of a voltage between the first electrode and the second electrode, the method comprising controlling the said voltage to change the shape of the meniscus.

Further features and advantages of the invention will become apparent from the following description of preferred embodiments of the invention, wherein.

Figure 1:
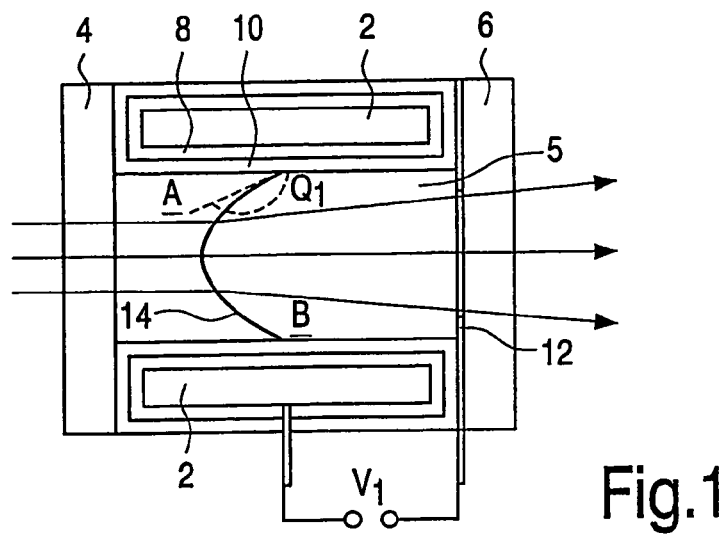
FIGS. 1 to 3 show an adjustable lens in accordance with an embodiment of the invention in schematic cross section.
Figure 2:
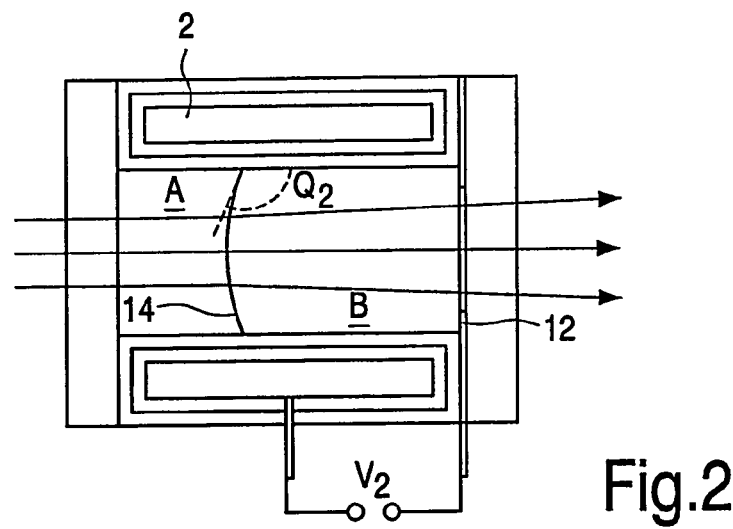
Figure 3:
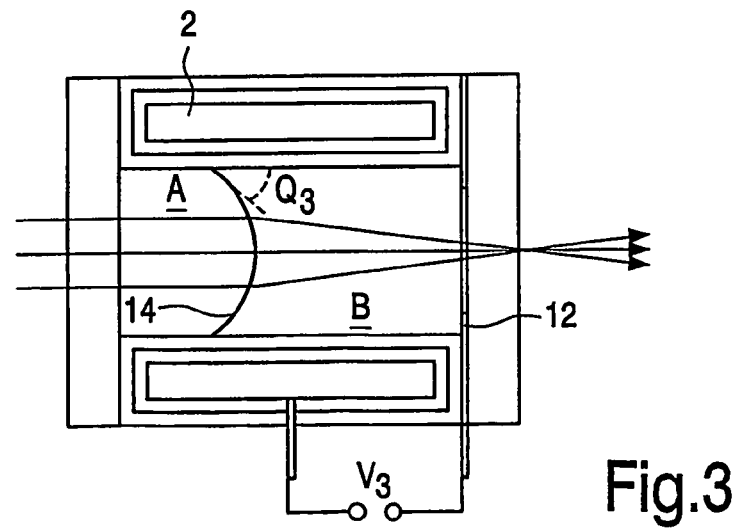

FIGS. 1 to 3 show a variable focus lens comprising a cylindrical first electrode 2 forming a capillary tube, sealed by means of a transparent front element 4 and a transparent back element 6 to form a fluid chamber 5 containing two fluids. The electrode 2 may be a conducting coating applied on the inner wall of a tube.

In this embodiment the two fluids consist of two non-miscible liquids in the form of an electrically insulating first liquid A, such as a silicone oil or an alkane, referred to herein further as "the oil", and an electrically conducting second liquid B, such as water containing a salt solution. The two liquids are preferably arranged to have an equal density, so that the lens functions independently of orientation, i.e. without dependence on gravitational effects between the two liquids. This may be achieved by appropriate selection of the first liquid constituent; for example alkanes or silicon oils may be modified by addition of molecular constituents to increase their density to match that of the salt solution.

Depending on the choice of the oil used, the refractive index of the oil may vary between 1.25 and 1.60. Likewise, depending on the amount of salt added, the salt solution may vary in refractive index between 1.33 and 1.48. The fluids in this embodiment are selected such that the first fluid A has a higher refractive index than the second fluid B.

The first electrode 2 is a cylinder of inner radius typically between 1 mm and 20 mm. The electrode 2 is formed from a metallic material and is coated by an insulating layer 8, formed for example of parylene. The insulating layer has a thickness of between 50 nm and 100 µm, with typical values between 1 µm and 10 µm. The insulating layer is coated with a fluid contact layer 10, which reduces the hysteresis in the contact angle of the meniscus with the cylindrical wall of the fluid chamber. The fluid contact layer is preferably formed from an amorphous fluorocarbon such as Teflon™ AF1600 produced by DuPont™. The fluid contact layer 10 has a thickness of between 5 nm and 50 µm. The AF1600 coating may be produced by successive dip coating of the electrode 2, which forms a homogeneous layer of material of substantially uniform thickness since the cylindrical sides of the electrode are substantially parallel to the cylindrical electrode; dip coating is performed by dipping the electrode whilst moving the electrode in and out of the dipping solution along its axial direction. The paralyne coating may be applied using chemical vapour deposition. The wettability of the fluid contact layer by the second fluid is substantially equal on both sides of the intersection of the meniscus 14 with the fluid contact layer 10 when no voltage is applied between the first and second electrodes.

A second, annular electrode 12 is arranged at one end of the fluid chamber, in this case, adjacent the back element. The second electrode 12 is arranged with at least one part in the fluid chamber such that the electrode acts on the second fluid B.

The two fluids A and B are non-miscible so as to tend to separate into two fluid bodies separated by a meniscus 14. When no voltage is applied between the first and second electrodes, the fluid contact layer has a higher wettability with respect to the first fluid A than the second fluid B. Due to electrowetting, the wettability by the second fluid B varies under the application of a voltage between the first electrode and the second electrode, which tends to change the contact angle of the meniscus at the three phase line (the line of contact between the fluid contact layer 10 and the two liquids A and B). The shape of the meniscus is thus variable in dependence on the applied voltage.

Referring now to FIG. 1, when a low voltage $V_1$, e.g. between 0 V and 20 V, is applied between the electrodes the meniscus adopts a first concave meniscus shape. In this configuration, the initial contact angle $\theta_1$ between the meniscus and the fluid contact layer 10, measured in the fluid B, is for example approximately 140°. Due to the higher refractive index of the first fluid A than the second fluid B, the lens formed by the meniscus, here called meniscus lens, has a relatively high negative power in this configuration.

To reduce the concavity of the meniscus shape, a higher magnitude of voltage is applied between the first and second electrodes. Referring now to FIG. 2, when an intermediate voltage $V_2$, e.g. between 20 V and 150 V, depending on the thickness of the insulating layer, is applied between the electrodes the meniscus adopts a second concave meniscus shape having a radius of curvature increased in comparison with the meniscus in FIG. 1. In this configuration, the intermediate contact angle $\theta_2$ between the first fluid A and the fluid contact layer 10 is for example approximately 100°. Due to the higher refractive index of the first fluid A than the second fluid B, the meniscus lens in this configuration has a relatively low negative power To produce a convex meniscus shape, a yet higher magnitude of voltage is applied between the first and second electrodes. Referring now to FIG. 3, when a relatively high voltage $V_3$, e.g. 150 V to 200 V, is applied between the electrodes the meniscus adopts a meniscus shape in which the meniscus is convex. In this configuration, the maximum contact angle $\theta_3$ between the first fluid A and the fluid contact layer 10 is for example approximately 60°. Due to the higher refractive index of the first fluid A than the second fluid B, the meniscus lens in this configuration has a positive power.

Note that, whilst achieving the configuration of FIG. 3 is possible using a relatively high power, it is preferred in a practical embodiment that a device including the lens as described is adapted to use only low and intermediate powers in the ranges described, that is to say that the voltage applied is restricted such that the electrical field strength in the insulating layer is smaller than 20 V/µm, and excessive voltages causing charging of the fluid contact layer, and hence degradation of the fluid contact layer, are not used.

Note furthermore that the initial, low voltage, configuration will vary in dependence on the selection of the liquids A and B, in dependence on their surface tensions). By selecting an oil with a higher surface tension, and/or by adding a component, such as ethylene glycol, to the salt solution which reduces its surface tension, the initial contact angle can be decreased; in this case the lens may adopt a low optical power configuration corresponding to that shown in FIG. 2, and an intermediate power configuration corresponding to that shown in FIG. 3. In any case, the low power configuration remains such that the meniscus is concave, and a relatively wide range of lens powers can be produced without using an excessive voltage.

Although the fluid A has a higher refractive index than fluid B in the above example, the fluid A may also have a lower refractive index than fluid B. For example, the fluid A may be a (per)fluorinated oil, which has a lower refractive index than water. In this case the amorphous fluoropolymer layer is preferably not used, because it might dissolve in fluorinated oils. An alternative fluid contact layer is e.g. a paraffin coating.

Figure 4:
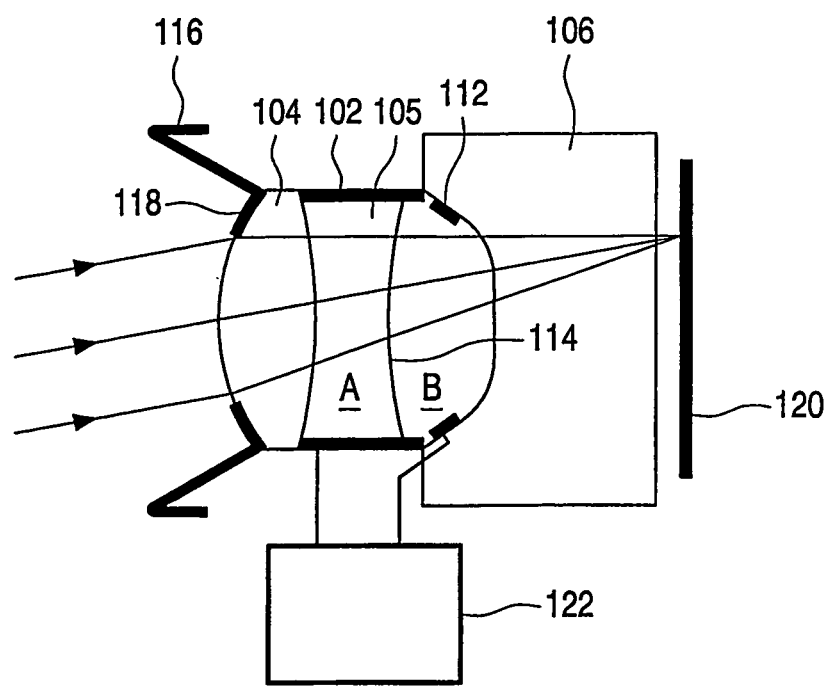
FIG. 4 shows an image capture device in accordance with an embodiment of the invention in schematic cross section.

FIG. 4 illustrates a variable focus image capture device including a lens in accordance with an embodiment of the present invention. Elements similar to that described in relation to FIGS. 1 to 3 are provided with the same reference numerals, incremented by 100, and the previous description of these similar elements should be taken to apply here.

The device includes a compound variable focus lens including a cylindrical first electrode 102, a rigid front lens 104 and a rigid rear lens 106. The space enclosed by the two lenses and the first electrode forms a cylindrical fluid chamber 105. The fluid chamber holds the first and second fluids A and B. The two fluids touch along a meniscus 114. The meniscus forms a meniscus lens of variable power, as previously described, depending on a voltage applied between the first electrode 102 and the second electrode 112. In an alternative embodiment, the two fluids A and B have changed position.

The front lens 104 is a convex-convex lens of highly refracting plastic, such as polycarbonate or cyclic olefin copolymer, and having a positive power. At least one of the surfaces of the front lens is aspherical, to provide desired initial focusing characteristics. The rear lens element 106 is formed of a low dispersive plastic, such as COC (cyclic olefin copolymer) and includes an aspherical lens surface which acts as a field flattener. The other surface of the rear lens element may be flat, spherical or aspherical. The second electrode 112 is an annular electrode located to the periphery of the refracting surface of the rear lens element 106.

A glare stop 116 and an aperture stop 118 are added to the front of the lens. A pixellated image sensor 120, such as a CMOS sensor array, is located in a sensor plane behind the lens.

An electronic control circuit 122 drives the meniscus lens, in accordance with a focus control signal, derived by focus control processing of the image signals, so as to provide an object range of between infinity and 10 cm. The control circuit controls the applied voltage between a low voltage level, at which focusing on infinity is achieved, and higher voltage levels, when closer objects are to be focused. When focusing on infinity, a concave meniscus with a contact angle of approximately 140° is produced, whilst when focusing on 10 cm, a concave meniscus with a contact angle of approximately 100° is produced.

The conducting second fluid, the insulating layer and the second electrode form an electrical capacitor, the capacitance of which depends on the position of the meniscus. The capacitance can be measured using a conventional capacitance meter. The optical strength of the meniscus lens can be determined from the measured value of the capacitance.

The lens is configured such that a low, non-zero, voltage is applied to focus the lens on an object at infinity (parallel incoming rays), so as to provide the capability to focus on infinity within reasonable manufacturing tolerances; if on the other hand the lens were to be configured such that focusing on infinity occurred when zero voltage is applied, more strict manufacturing tolerances would have to be applied.

The front lens element 104 is preferably formed as a single body with a tube holding the electrode 102 on its inner surface and closed off by the rear lens 106 to form a sealed unit. The second lens element 106 may be extended, in relation to that shown in FIG. 4, and the flat rear surface of the lens element 106 may be replaced by an angled mirror surface, preferably angled at 45°, to allow the image sensor 120 to be placed below the lens, in order to reduce the dimensions of the lens.

The fluid chamber 105 may be provided with an expansion chamber to accommodate volume changes due to thermal expansion of the fluids. The expansion chamber may be a flexible membrane in one of the walls of the fluid chamber.

The inner surfaces of the front lens 104 and the rear lens 106 may be coated with a protective layer to avoid incompatibility of the material from which the lenses are made with the fluids A and B. The protective layer may also have anti-reflection characteristics.

Figure 5:
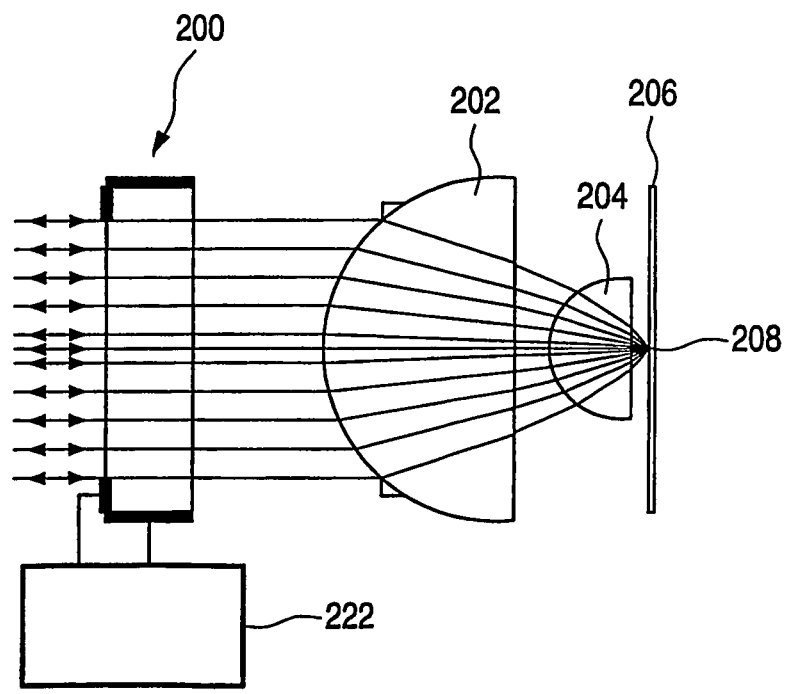
FIG. 5 shows an optical scanning device in accordance with an embodiment of the invention in schematic cross section.

FIG. 5 shows elements from an optical scanning device containing a lens in accordance with an embodiment of the invention. The device is for recording and/or playback from an optical disk 206, for example a dual layer digital video recording (DVR) disk (see for instance the article by K. Schep, B. Stek, R. van Woudenberg, M. Blum, S. Kobayashi, T. Narahara, T. Yamagami, H. Ogawa, "Format description and evaluation of the 22.5 GB DVR disc", Technical Digest, ISOM 2000, Chitose, Japan, Sep. 5–8, 2000). The device includes a compound objective lens, for instance having a numerical aperture of 0.85, including a rigid front lens 202 and a rigid rear lens 204, for instance as described in International patent application WO 01/73775, for focusing the incoming collimated beam, for instance having a wavelength of 405 nm, consisting of substantially parallel rays, to a spot 208 in the plane of an information layer currently being scanned.

In dual layer DVR disks the two information layers are at depths of 0.1 mm and 0.08 mm; they are thus separated by typically 0.02 mm. When refocusing from one layer to the other, due to the difference in information layer depth, some 200 m$\lambda$ of unwanted spherical wavefront aberration arises, which needs to be compensated. One way to achieve this is to change the vergence of the incoming beam using a mechanical actuator, for example moving a collimator lens in the device, which is relatively expensive. Another approach is to use a switchable liquid crystal cell, which is also a relatively expensive solution.

In this embodiment, a switchable variable focus lens 200 similar to that described in relation to FIGS. 1 to 3 is used. In this embodiment, the oil chosen is polydimethyl (8–12%)-phenylmethylsiloxane copolymer, and a salt water solution is used as the conducting liquid. Each of the liquids, when the lens 200 is arranged with a planar meniscus, has a thickness of approximately 1 mm.

The device includes an electronic control circuit 222 for applying one of two selected voltages to the electrodes of the lens 200 in dependence on the information layer currently being scanned. In one configuration, during the scanning of the information layer depth of 0.08 mm, a relatively low selected voltage is applied to produce a meniscus curvature of radius R=21.26 mm. In the other configuration, during the scanning of the information layer depth of 0.1 mm, a relatively high selected voltage is applied to produce a planar meniscus curvature. As a result, the root mean square value of the wavefront aberration can be reduced from 200 m$\lambda$ to 18 m$\lambda$. Note that a similar effect can be obtained using different combinations of meniscus curvatures, since only a variation in lens power is required; furthermore the difference in lens power can also be achieved with larger movements in the meniscus by making the refractive indices of the two liquids more similar.

Note, in relation to all the above embodiments, the electrode is itself preferably cylindrical, but some variation from a perfect cylinder is possible, e.g. slightly conical. However, the cylinder should preferably remain substantially cylindrical, namely where the fluid contact layer has a linear cross section, i.e. the layer forms straight lines in a cross section of the cylinder, where the axis of the cylinder lies in the cross section. The linear cross section should be parallel to the axis of the electrode at least to within 10 degrees, more preferably at least to within 1 degree. A cylindrical electrode can be made using conventional, cheap tubing having a cross section which is parallel to the axis within 0.1 degree and a smooth inner wall on which the various layers can be deposited. The possibility to use such tubing gives the lens according to the invention a cost advantage. The fluid contact layer may itself not be perfectly linear; however any non-linearity is preferably limited such that the non linearity causes a difference in radial extent less than one tenth, more preferably less than one twentieth, of the axial extent of the electrode.

The above embodiments are to be understood as illustrative examples of the invention. Further embodiments of the invention are envisaged. For example, the first fluid may consist of a vapour rather than an insulating liquid. The second fluid may be a fluid having a lower surface tension than the first fluid. In that case the shape of the meniscus at low applied voltages will be convex.

It is to be understood that any feature described in relation to one embodiment may also be used in other of the embodiments.

Furthermore, equivalents and modifications not described above may also be employed without departing from the scope of the invention, which is defined in the accompanying claims.

The invention claimed is:

1. A variable focus lens including
   a substantially cylindrical fluid chamber having a cylinder wall, the fluid chamber including a first fluid (A) and an axially displaced second fluid (B), the fluids being non-miscible, in contact over a meniscus (14) and having different indices of refraction,
   a fluid contact layer (10) arranged on the inside of the cylinder wall,
   a first electrode (2) separated from the first fluid and second fluid by the fluid contact layer,
   a second electrode (12) acting on the second fluid,
   the fluid contact layer having a wettability by the second fluid which varies under the application of a voltage between the first electrode and the second electrode, such that the shape of the meniscus varies in dependence on the said voltage,
   wherein the wettability of the fluid contact layer by the second fluid is substantially equal on both sides of the intersection of the meniscus with the contact layer when no voltage is applied between the first and second electrodes.

2. A lens according to claim 1, wherein the inner surface of the fluid contact layer has a linear cross-section, and wherein the linear cross section is parallel to the axis of the substantially cylindrical shape of the surface to within 10 degrees.

3. A lens according to claim 1, wherein the first fluid includes an insulating liquid and the second fluid includes a conducting liquid.

4. A lens according to claim 1, wherein the first fluid includes a vapour and the second fluid includes a conducting liquid.

5. A lens according to claim 1, wherein the lens is arranged to produce a meniscus shape which is concave when viewed from the second fluid, the shape becoming less concave at increasing magnitude of voltage applied between the first and second electrodes.

6. A lens according to claim 1, wherein the fluid contact layer is a substantially homogeneous layer of uniform thickness.

7. A lens according to claim 1, wherein said first electrode is substantially cylindrical.

8. A lens according to claim 1, wherein said first fluid has a larger refractive index than said second fluid and wherein the lens is a compound lens comprising at least one fixed lens element (104) providing a positive lens power, such that the compound lens has a positive lens power when the meniscus is convex in relation to the first fluid.

9. An optical device comprising a lens according to claim 1, the device comprising means defining a focusing plane (120) wherein the lens is arranged such that when radiation consisting of parallel rays is input and a non-zero voltage is applied between the first and second electrodes, the radiation is focused on the focusing plane.

10. An image capture device comprising a lens according to claim 1.

11. An optical scanning device for scanning an optical record carrier, comprising a lens according to claim 1.

12. An optical scanning device according to claim 1, wherein said lens is arranged to correct for spherical aberrations arising during the scanning of different information layer depths in optical record carriers being scanned.

13. A method of operating a variable focus lens including
   a substantially cylindrical fluid chamber having a cylinder wall, the fluid chamber including a first fluid (A) and an axially displaced second fluid (B), the fluids being non-miscible, in contact over a meniscus (14) and having different indices of refraction,
   a fluid contact layer (10) arranged on the inside of the cylinder wall,
   a first electrode (2) separated from the first fluid and second fluid by the fluid contact layer,
   a second electrode (12) acting on the second fluid,
   the wettability of the fluid contact layer by the second fluid being substantially equal on both sides of the intersection of the meniscus with the contact layer when no voltage is applied between the first and second electrodes,
   the wettability of the fluid contact layer by the second fluid varying under the application of a voltage between the first electrode and the second electrode,
   the method comprising controlling the said voltage to change the shape of the meniscus.

14. A method according to claim 13 wherein said method comprises varying said voltage to produce a meniscus shape which is concave when viewed from the second fluid.

15. A method according to claim 13, wherein said method further comprises varying said voltage to produce a meniscus shape which is convex when viewed from second fluid.

16. A method according to claim 15, wherein said meniscus has a contact angle with the fluid contact layer of between 100 and 140 degrees.

* * * * *